(12) United States Patent
Esashi et al.

(10) Patent No.: US 6,936,015 B2
(45) Date of Patent: Aug. 30, 2005

(54) ACTIVE GUIDE WIRE AND METHOD OF MAKING THE SAME

(75) Inventors: Masayoshi Esashi, 11-9, Yagiyamaminami 1-chome, Taihaku-ku, Sendai-shi, Miyagi 982-0807 (JP); Yoichi Haga, 2-5-903, Kokubun-cho 1-chome, Aoba-ku, Sendai-shi, Miyagi 980-0803 (JP); Takashi Mineta, Yamagata (JP)

(73) Assignees: Masayoshi Esashi, Sendai (JP); Yoichi Haga, Sendai (JP)

( * ) Notice: Subject to any disclaimer, the term of this patent is extended or adjusted under 35 U.S.C. 154(b) by 365 days.

(21) Appl. No.: 10/162,896

(22) Filed: Jun. 6, 2002

(65) Prior Publication Data

US 2003/0097080 A1 May 22, 2003

(30) Foreign Application Priority Data

Nov. 22, 2001 (JP) .......................... 2001-358453

(51) Int. Cl.$^7$ ............................. A61B 5/00; A61M 25/00
(52) U.S. Cl. ........................................ 600/585; 604/528
(58) Field of Search ............................... 600/433–435, 600/585; 604/264, 523, 528–532

(56) References Cited

U.S. PATENT DOCUMENTS

| | | | | |
|---|---|---|---|---|
| 4,944,727 A | * | 7/1990 | McCoy ........................ | 604/528 |
| 5,211,183 A | * | 5/1993 | Wilson ........................ | 600/585 |
| 5,415,633 A | * | 5/1995 | Lazarus et al. .......... | 604/95.05 |
| 6,329,069 B1 | * | 12/2001 | Azizi et al. ................. | 428/600 |
| 6,672,338 B1 | * | 1/2004 | Esashi et al. ............... | 138/119 |
| 2003/0199818 A1 | * | 10/2003 | Waldhauser et al. ..... | 604/95.05 |

FOREIGN PATENT DOCUMENTS

| | | |
|---|---|---|
| JP | 2000-233027 | 8/2000 |
| JP | 2001-279500 | 10/2001 |

OTHER PUBLICATIONS

Takashi Mineta et al. "An Active Guide Wire With Shape Memory Alloy Bending Actuator Fabricated By Room Temperature Process" Transducers '01 Eurosensors XV, The 11$^{th}$ International Conference on Solid–State Sensors and Actuators, Munich, Germany, Jun. 10–14, 2001, vol. 1, pp. 698–701.

Shuxiang Guo et al. "A Study on Active Catheter System (Structure, Experimental Results and Characteristic Evaluation of Active Catheter with Multi D.O.F)." JRSJ(Japan Robot Society Journal), vol. 14, No. 6, Sep. 1996, pp. 820–835 (Abstract Only).

* cited by examiner

*Primary Examiner*—Charles Marmor
(74) *Attorney, Agent, or Firm*—Westerman, Hattori, Daniels, and Adrian LLP

(57) ABSTRACT

An active guide wire (1) that can be used in a narrow blood vessel in a complicate vascular system such as intracerebral is disclosed as well as a method of making the same. The active wire comprises a bias coil spring (3); an outer tube (4) having the bias coil spring (3) sheathed therewith and providing an external wall for the active wire guide (1); and a shape memory alloy (SMA) actuator (5) in the form of a flat sheet anchored in and securely connected to the outer tube (4), wherein the flat sheet SMA actuator (5) is shape memorized so as to bend in a direction of the thickness of the flat sheet and has a shape running zigzag longitudinally thereof. The actuator (5) is energized with an electric current and thereby heated to have its leading end bent.

4 Claims, 13 Drawing Sheets

Prior Art

Prior Art

ACTIVE GUIDE WIRE AND METHOD OF MAKING THE SAME

BACKGROUND OF THE INVENTION

1. Field of the Invention

The present invention relates to an active guide wire for a catheter used in medical diagnosis or treatment as carried into a blood vessel and, in particular, to an improved guide wire that can be used for guiding the catheter to locate it at a desired site in narrow blood vessels of a complex vascular system such as intracerebral. The invention further relates to a method of making such an active guide wire.

2. Description of the Prior Art

The use of a guide wire to guide a catheter inserted in a blood vessel towards and through an affected or a potentially affected part has been known. In such use, the catheter into which the guide wire is inserted is allowed to orient in a desired direction by causing the leading end of the guide wire to bend to orient in that direction.

FIG. 11 is a view that diagrammatically illustrates how the catheter is advanced in blood vessels with the direction of its orientation controlled. While it is ideal to provide the catheter 111 itself with a bending drive mechanism at its leading end as shown, the catheter 111 can work equivalently to achieve an equivalent effect if a guide wire 112 is provided with a bending drive mechanism at its leading end is loaded in the catheter 111 as shown in FIG. 12. Even if the bending drive mechanism at the leading end of the guide wire is a bending mechanism capable of bending the leading end only in one direction, the bending action combined with a twisting operation 113 by the operator at the proximal side of the guide wire as shown allows its distal or leading end to orient in any direction as desired.

In order to guide the catheter at will along a complicate and fine duct line such as in the cerebrovascular system, the guide wire is desirable to be 0.5 mm or less in diameter and is required to possess an active drive function that is capable of bending the leading end and restoring it to be straightened as occasions demand. Furthermore, inasmuch as the vascular wall of aneurysm and those of a lesion such as stenosis is often extremely fragile, so that the region of the lesion or those vascular walls may not be injured by the guide wire, the wire guide must be made extremely low in its lateral and longitudinal stiffness.

In the medical site where it is necessary to guide the catheter at will along a fine and fragile blood vessel in a complicate vascular system such as pathologically changed cerebral blood vessels, an active guide wire small in diameter and low in stiffness if realized can be combined with a variety of existing catheters and is thereby expected to achieve great effects.

Conventional active guide wires with an active drive mechanism include, for example, one with a structure proposed by the present inventors as disclosed in our earlier Japanese Patent Application No. H10-355170 (JP 2000-233027 A).

The active guide wire disclosed there comprises as shown in FIG. 13, a bias coil spring 131 of radius r, and an actuator 132 disposed as fastened to the bias coil spring 131. The actuator 132 is made of a wire of a shape memory alloy (SMA) coiled and shape memorized so that it expands and contracts with a large stroke longitudinally of the coil; when heated by having an electric current passed therethrough the actuator 132 contracts or shrinks longitudinally thereof.

With this makeup, heating the actuator 132 by passing an electric current therethrough causes the actuator 132 to shrink, thereby producing a shrinking force F and thus causes the leading end of the active guide wire to bend with bending moment M=F×r. And removing the electric current permits the leading end of the active guide wire under the restoring force by the bias coil spring 131 to restore its straightness.

It has been found, however, that using this makeup to form an active guide wire that is small in diameter (=2r) makes it hard to enough bend the leading end of the active wire guide for the reason that reducing the radius r of the bias coil spring 131 reduces the bending moment M.

Attempting to hold the bending moment M needed to enough bend the leading end of the active guide wire calls for increasing the shrinking force F of the actuator 132. Attempting to increase the shrinking force of the actuator 132 in turn requires making thicker the wire diameter of the coiled wire made of a shape memory alloy. Making the wire diameter thicker of the coiled wire 132, however, makes it larger in both its lateral and longitudinal stiffness.

Also, this makeup in which the actuator 132 is allowed to shrink requires the bias coil spring 131 to be axially of not less than a certain stiffness such that the shrinkage of the actuator 132 may not shrink or buckle the active guide wire as a whole.

Thus, this makeup is found to be hard to satisfy simultaneously the reduced diameter which is required for the active guide wire used to carry the catheter in a narrow blood vessel of a complicate vascular system such as intracerebral and to guide it to reach a desired site for diagnosis or treatment, and the adequate stiffness which is required not to injure a pathologically changed vascular wall.

The active guide wire may utilize another makeup proposed by the present inventors and disclosed in earlier Japanese Patent Application No. 2000-092209. The makeup of the active guide wire there disclosed differs from the makeup disclosed in JP 2000-233027 A in that the actuator made of a shape memory alloy is in the form of an elongate flat sheet shaped to run zigzag along the axis thereof. The actuator is shape memorized so that when heated with an electric current passed therethrough it shrinks along the axis thereof with a large stroke.

With this makeup, as in that described in JP 2000-233027 A, reducing the guide wire in diameter must result in an increase in stiffness of the actuator to keep the enough bending moment M. Furthermore, the bias spring coil must again be axially of not less than a certain stiffness to avoid shrinking or buckling as the whole. Consequently, this makeup, too, makes it hard to bring into reality, not only the reduced diameter which is required for the active guide wire used to carry the catheter in a narrow blood vessel of a complicate vascular system such as intracerebral and to guide it to reach a desired site for diagnosis or treatment, but also the adequate stiffness which is required not to injure pathologically changed vascular walls.

Thus, while active guide wires of these prior designs are each highly useful when used to carry a catheter in an aorta, a renal artery or the like blood vessel that is relatively thick itself and in wall thickness, said prior guide wires used in a cerebral or a pathologically changed blood vessel may potentially injure the blood vessel.

BRIEF SUMMARY OF THE INVENTION

It is accordingly an object of the present invention to provide an active guide wire that is not only small in diameter as required for the active guide wire used to carry the catheter in a narrow blood vessel of a complicate vascular system such as intracerebral and to guide it to reach a desired site for diagnosis or treatment, but also having the adequate stiffness not to injure a pathologically changed vascular wall. It is also an object of the present invention to provide a method of making such an active guide wire.

In order to achieve the objects mentioned above, there is provided in accordance with the present invention an active guide wire which comprises: a bias coil spring; an outer tube having the bias coil spring sheathed therewith and providing an external wall for the active guide wire; and a shape memory alloy (SMA) actuator in the form of a flat sheet anchored in and securely connected to the said outer tube, wherein the said flat sheet SMA actuator is shape memorized so as to bend in a direction of the thickness of the said flat sheet and has a shape running zigzag longitudinally thereof, namely along the long axis thereof.

Preferably, the said bias coil spring is composed of an electrically conductive elastic material, and the said outer tube is composed of a polymeric material.

The active guide wire mentioned above specifically further includes an electrically conductive spacer whereby an end portion of the said actuator and an end portion of the said bias coil spring are brought together, a plurality of electrically nonconductive spacers whereby a plurality of intermediate regions of the said actuator are fastened to, but held not in electrical contact with, a plurality of intermediate regions of the said bias coil spring, respectively; a further electrically nonconductive spacer whereby a base portion of the said actuator is fastened to, but held not in electrical contact with, a base portion of the said bias coil spring; and a lead conductor connected to the base portion of said actuator.

With the active guide wire constructed as mentioned above, applying a voltage between the lead conductor and the base portion of the bias coil spring draws an electric current flowing via the bias coil spring and the conductive spacer through the actuator, thereby electrically heating the actuator. Heated to reach the critical or transformation temperature of the shape memory alloy, the actuator and hence the active guide wire is allowed to bend. Removing the voltage causes the actuator to cool to a temperature below the critical temperature of the shape memory alloy and thus to lose the bending force. Then, under the restoring force exerted by the bias coil spring, the active guide wire is allowed to restore its original straight shape.

Since the flat sheet SMA actuator is shape memorized so as to bend in a direction of the thickness of the flat sheet, the bending force is produced in a direction perpendicular or transverse to the axis of the actuator and over the entire surface of the flat sheet, thus permitting the active guide wire to bend regardless of the coil diameter of the bias coil spring. Since the active guide wire with the bias coil spring as slender as having a coil diameter of 0.5 mm or less can be bent without increasing the thickness of flat SMA sheet, the actuator can be reduced in stiffness. Moreover, the shape of the flat sheet SMA actuator having a shape running zigzag longitudinally thereof makes its stiffness in both transverse and longitudinal directions remarkably low.

Furthermore, the flat sheet SMA actuator designed to bend in a direction of the thickness of the flat sheet prevents the bias coil spring from shrinking in its longitudinal direction, thus preventing the active guide wire itself from shrinking or buckling while reducing the bias coil spring as well in stiffness.

These advantageous effects make it possible to realize an active guide wire that is reduced not only in diameter but also in stiffness both transverse and longitudinal and thus free from injuring a fragile vascular wall if collided thereby.

Also, forming the bias coil spring from a electrically conductive elastic material not only permits it to carry electric current but also makes it possible to fabricate it with a desired coil diameter and stiffness. For example, if formed from a thin stainless steel wire, an extra-slender and low stiffness bias coil spring can be prepared which can be for cerebral vascular tracts.

Further, the outer tube made in a coating of a polymeric material such as polyurethane is biocompatible and is well suitable for use in a blood vessel.

Also, the actuator, provided that its end portion is electrically connected to the end portion of the bias coil spring and its intermediate and base portions are electrically insulated from the bias coil spring, advantageously forms a series circuit with the latter which can adequately carry an electric current applied for directly heating the actuator without requiring any additional intricate electrical circuit component for providing the electrical heating current.

The present invention also provides a method of making an active guide wire, which method comprises the steps: a) fabricating a flat sheet, shape memory alloy (SMA) actuator; b) fabricating an actuator/spacer assembly from the said flat sheet SMA actuator, spacers and a lead conductor; c) fabricating an outer tube from a bias coil spring and a liquid polymer; and d) fabricating a said active guide wire from the said actuator/spacer assembly fabricated in step b and the said outer tube fabricated in step c.

In the method mentioned above, step b preferably includes putting a tubular conductive spacer over an end portion of the said flat sheet SMA actuator, putting a plurality of tubular nonconductive spacers over a plurality of intermediate regions of the said actuator, respectively, which are mutually spaced apart by a preselected distance, putting a further tubular nonconductive spacer over a base portion of the said actuator, the said tubular spacers each having a hollow inner space, filling the hollow inner spaces of the said tubular spacers at the said end portion and said base portion each with a room temperature setting, conductive epoxy resin, filling the hollow inner spaces of the said tubular spacers at said intermediate regions with a room temperature, nonconductive epoxy resin, and permitting said epoxy resin to set at a room temperature. This specific method permits the actuator to be connected to the outer tube with ease both electrically and mechanically.

Also in the method mentioned above, step c preferably includes inserting a silicon tube into the said bias coil spring, applying a liquid polymer over the said bias coil spring and the said silicon tube and drying the liquid polymer to form a coating thereof over them, and applying a force between an end of said silicone tube and the said polymer coating to extract the said silicon tube and thereby to produce the said outer tube. This specific method permits fabricating the outer tube in the form of a bellows in which the bias coil spring is sheathed with the polymer coating having a uniform and adequate thickness.

Also in the method mentioned above, step d preferably includes inserting the said actuator/spacer assembly fabricated in step b into the said outer tube fabricated in step c, securely connecting the said conductive spacers to the said outer tube with room temperature setting, conductive epoxy resin, removing those portions of the polymer which are located over the said nonconductive spacers, securely connecting the said nonconductive spacers and the said bias coil spring thus exposed to the said outer tube with room temperature setting, nonconductive epoxy resin, applying a liquid polymer over the said outer tube having the said actuator/spacer assembly fastened thereto and drying the same.

This specific method permits the actuator/spacer assembly and the outer tube to be joined together with ease and accuracy to assemble the active guide wire. Also, the specific method by applying a liquid polymer over the outer tube gives rise to a smooth outer tube surface and at the same time makes the required electrical insulation perfect.

According to another specific feature in the method aspect of the present invention, step a of fabricating the flat sheet SMA actuator includes drawing out a shape memorized SMA sheet into a flat sheet at a temperature below the critical temperature of the SMA, and machining the flat SMA sheet by laser ablation into the said actuator shape.

In this specific method, mounting the SMA sheet on the worktable in a laser ablation apparatus and effecting a scan movement relatively between a laser beam and the worktable on the basis of the actuator shape stored in a computer permits the SMA sheet to be machined into the target actuator shape. Hence the specific method allows the actuator to be manufactured at a low cost, compared with the method such as photolithography and electrochemical etching, when production amount is small. Another advantage of this specific method is its capability of manufacturing at a temperature below the critical temperature of the SMA, which eliminates the possibility of the actuator to be bent in the course of its manufacture. Consequently, it is made possible for the active guide wire extremely small in structure to be reliably manufactured at a low cost.

BRIEF DESCRIPTION OF THE DRAWINGS

The present invention will better be understood from the following detailed description and the drawings attached hereto showing certain illustrative forms of embodiment of the present invention; in this connection, it should be noted that such forms of embodiment illustrated in the accompanying drawings hereof are intended in no way to limit the present invention but to facilitate an explanation and understanding thereof. In the drawings.

DETAILED DESCRIPTION

Figure 1:
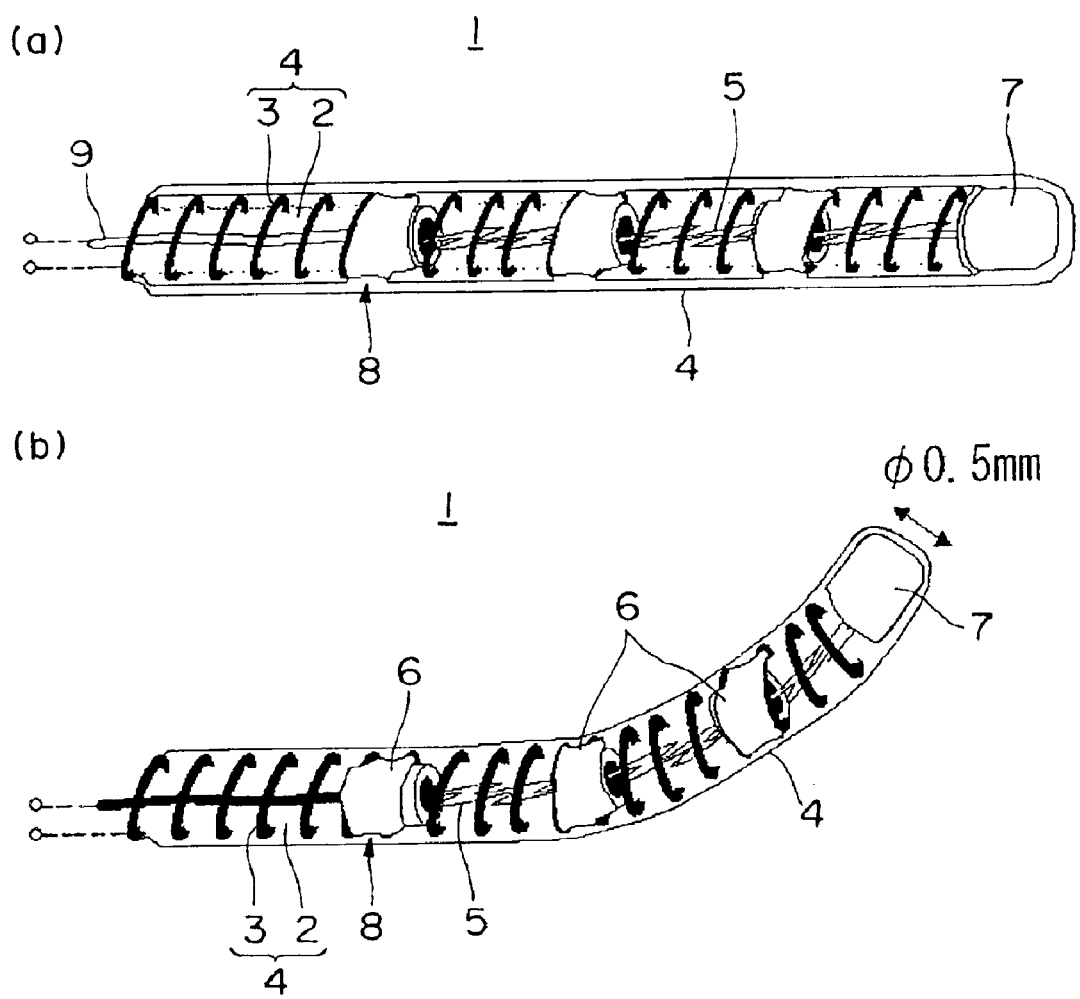
FIGS. 1A and 1B are views in part perspective illustrating the makeup and the operation of an active guide wire according to the present invention wherein FIG. 1A indicates the state that the active guide wire is unactuated and FIG. 1B indicates the state that it is actuated to have its leading end bent.

The present inventors have created an active guide wire of about 0.5 mm in outer diameter provided with a simple mechanism capable of bending its leading end in one direction. The active guide wire is made by combining together a flat sheet shape memory alloy (SMA) actuator (hereinafter referred to as "bending actuator" or "SMA actuator") fabricated from an SMA sheet of 35 μm in thickness made of a NiTi alloy and a bellows outer tube having a bias coil spring sheathed with a polyurethane layer.

A form of implementation of the present invention is described below, first with reference to FIGS. 1A and 1B, which are views in part perspective illustrating the makeup and the operation of an active guide wire according to the present invention wherein FIG. 1A indicates the state that the active guide wire is unactuated and FIG. 1B indicates the state that it is actuated to have its leading end bent.

The active guide wire 1 indicated by reference character 1 comprises the SMA actuator, the bias coil spring and the bellows outer tube, indicated by reference characters 5, 3 and 4, respectively. The bias coil spring 3, which is electrically conductive, is sheathed with the polyurethane layer indicated by reference character 2 to form the bellows outer tube 4. The SMA actuator 5 is securely connected to the bellows outer tube 4 via glass pipes 6 which act as nonconductive spacers. The leading end of the actuator 5 is securely connected to the bias coil spring 3 via a brass pipe 7 which acts as a conductive spacer. The SMA actuator 5 has a base 8 connected to a conductor 9 for applying an electric current thereto. Thus, the SMA actuator 5 is designed to be heated directly with the electric current passed therethrough via the current conducting conductor 9, and the coil spring 3.

And, heating the SMA actuator 5 to a temperature, for example, of 75° C. by current conduction causes it to bend, thus causing it to actuate to bend the leading end of the active guide wire 1 as shown in FIG. 1B, and terminating the current conduction allows the biasing force of the bias coil spring 3 to cause the leading end of the active guide wire 1 to restore its unactuated state as shown in FIG. 1A. Thus, the active guide wire 1 is given a mechanism whereby it is bent in one direction.

Figure 2:
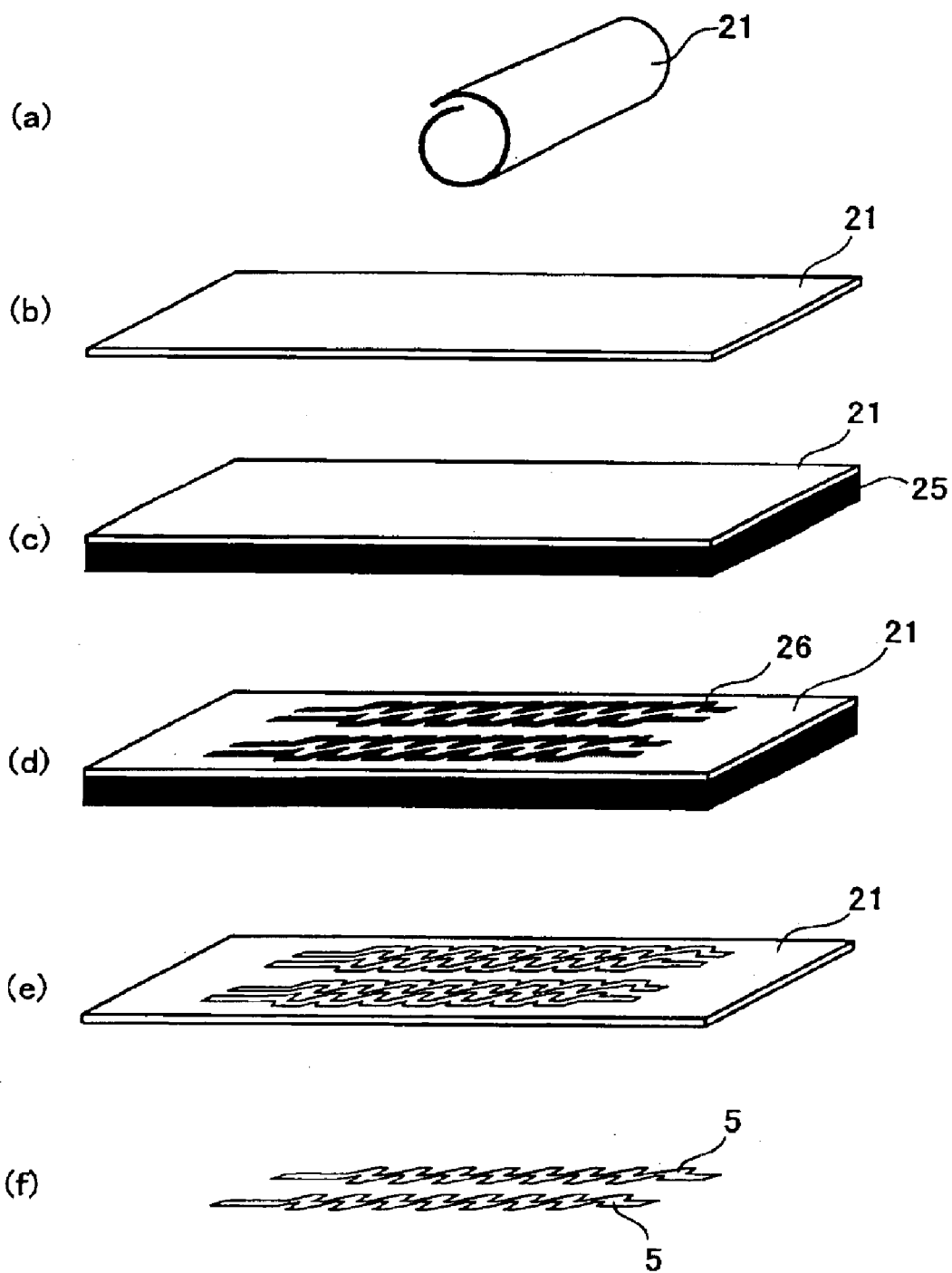
FIG. 2 is a flow chart illustrating a process of making a shape memory alloy (SMA) actuator in the active guide wire shown in FIG. 1.

Mention is next made of the SMA actuator with reference to FIG. 2, which is a flow chart illustrating a process of making the SMA actuator. First in step (a), an SMA sheet 21 of 35 μm in thickness is formed by heat treatment into, and thereby memorized with, a rolled shape of a radius φ of 2.5 mm. Then in step (b), the rolled SMA sheet 21 is drawn out at a room temperature into a flat or planar form. And the flattened SMA sheet 21 then is processed in a photolithographic and an electrolytic treatment as mentioned below. To prevent deformation into the rolled shape, steps thereafter are carried out at a temperature lower than the transformation temperature (70° C.) of the SMA.

Figure 3:
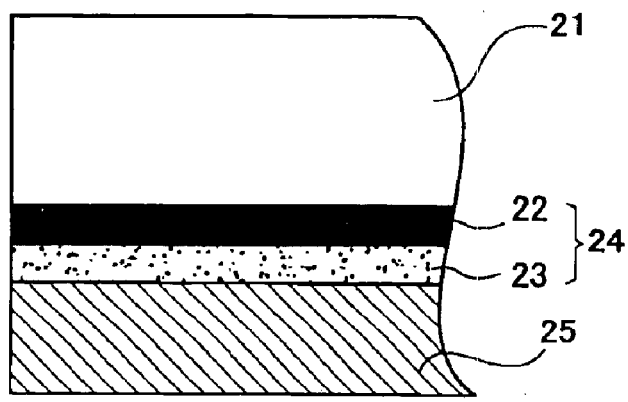
FIG. 3 is an enlarged view in cross section illustrating an intermediate layer and a copper electroplated layer provided on the backside of an SMA sheet in the course of forming the actuator.

In step (c), as shown in FIG. 3 the SMA sheet 21 is formed on its back side by sputtering with a Cu/Ni layer 24 as an intermediate layer comprising a Ni layer 22 and a Cu layer 23 each of 0.1 $\mu$m in thickness and then thereon at a room temperature with an electrically conductive dummy layer of Cu 25 having a thickness of 10 $\mu$m or more. While an electroplated Cu layer 25 or film itself has adhesive properties inferior to those of a Ni layer (a growth temperature of 45° C.), the presence of the sputtered intermediate Cu/Ni layer 24 here permits the electroplated Cu layer 25 to adhere to the SMA sheet 21 with enough bond strength.

Figure 4:
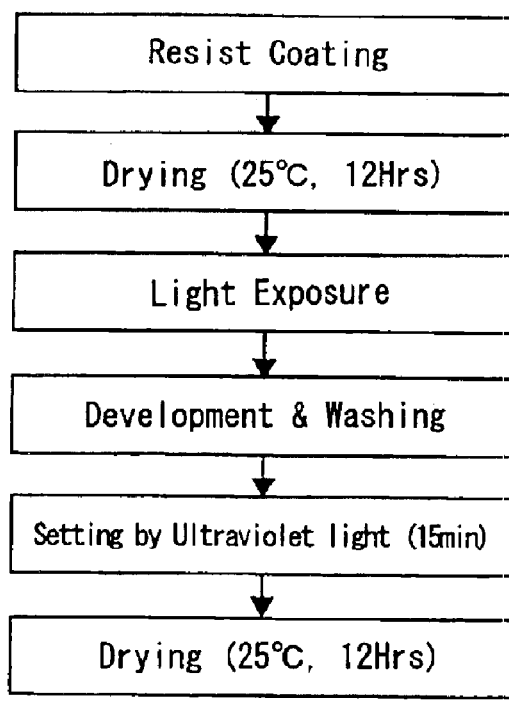
FIG. 4 is a flow chart illustrating the process of lithography in the course of forming the actuator.

Next, photolithography is conducted on the SMA sheet 21 in step (d). Referring to FIG. 4 showing the photolithographic process in a flow chart, the SMA sheet 21 after having a resist (made of OMR supplied from Tokyo Oyo Kagaku, Kabushiki Kaisha) applied on its front face with a thickness of about 1.5 $\mu$m is dried at a temperature of 25° C. for a period of 12 hours. Then, the SMA sheet with a negative mask patterned after the shape of the SMA actuator is exposed to ultraviolet light and thereafter subjected to development and washing to form thereon a resist pattern 26 of the SMA actuator of the shape shown in FIG. 2(d). The resist pattern is then cured by being irradiated with an ultraviolet ray of 100 mW/cm$^2$ for a period of 15 minutes, and thereafter dried at a temperature of 25° C. for a period of 12 hours.

Next, the SMA sheet 21 with the mask of the resist pattern 26 is dipped in a liquid electrolyte containing sulfuric acid and methanol in which it is electrochemically etched from its front side through its thickness until etching reaches the Cu layer 25 on its back side. While the resist pattern 26 formed at the room temperature is apparently not completely polymerized, it is seen to have enough resistance to electrochemical etching.

Next in step (e) shown in FIG. 2, dipped in concentrated nitric acid, the electroplated Cu layer 25, the sputtered Cu/Ni layer and the resist pattern 26 are removed. Finally, etching pattern come-off protection twigs are detached from the formed SMA sheet to give rise to SMA actuators 5 as shown in FIG. 2(f).

Figure 5:
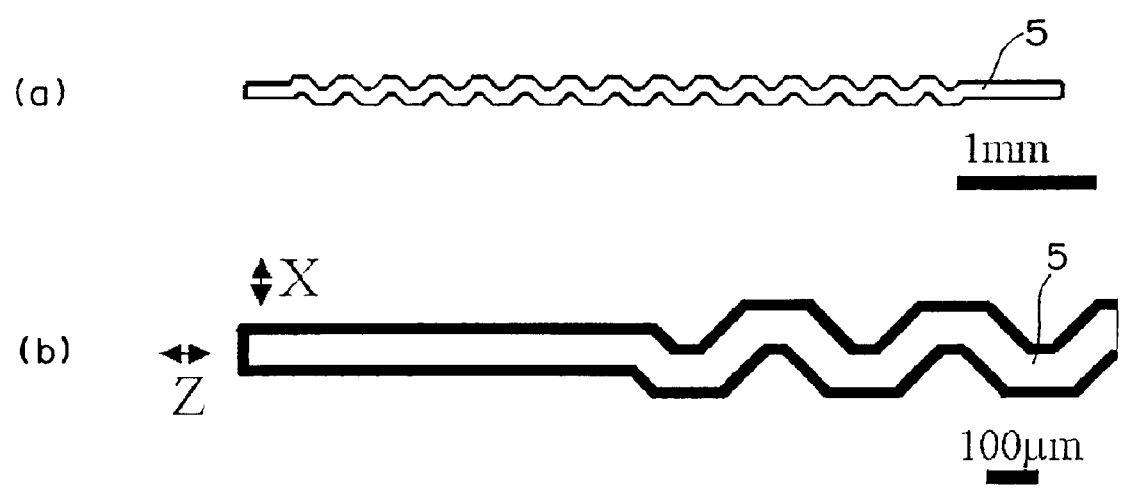
FIG. 5 is a view illustrating the shape of an SMA actuator thus fabricated.

The SMA actuator 5 thus fabricated is shown in FIG. 5 in a general view at (a) and in a view of its essential parts at (b). So that the active guide wire on coming into contact with a vascular wall may not injure it, the SMA actuator 5 is shaped into a zigzag pattern, thereby reducing the stiffness against longitudinal compression (in the direction of Z-axis) and transverse bending (in the direction of x-axis) to minimum. The zigzag pattern runs zigzag along a sine curve having a period of 340 $\mu$m and an amplitude of 60 $\mu$m.

Figure 14:
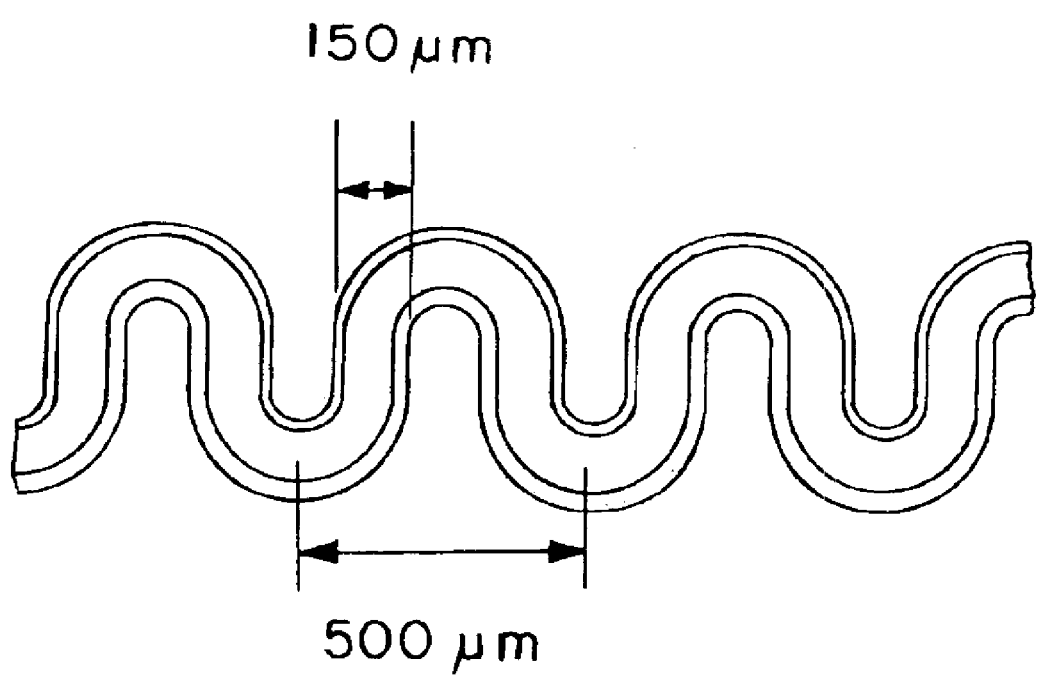
FIG. 14 is a view showing an actuator fabricated by laser ablation.
Figure 15:
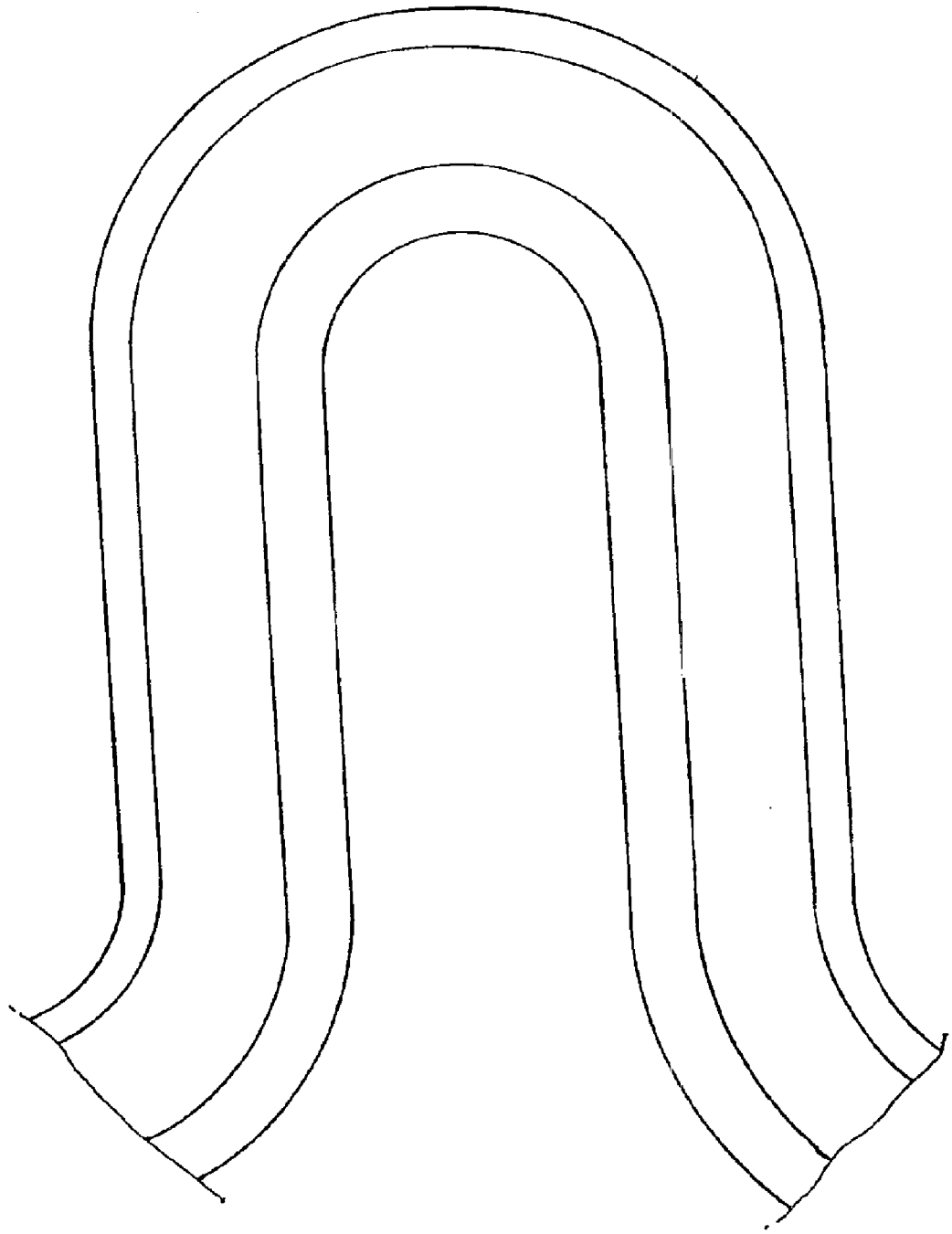
FIG. 15 is an enlarged view showing the actuator fabricated by laser ablation.

Mention is next made of a method of making the actuator using laser ablation. Referring again to FIG. 2, an SMA sheet 21 in step (a) is formed by heat treatment into, and thereby shape memorized with, a rolled shape as mentioned previously. Then in step (b), the rolled SMA sheet 21 is drawn out at a room temperature into a flat or planar form. And the flattened SMA sheet 21 then is mounted in a laser ablation apparatus, in which either the laser beam or the worktable is movable relative to the other fixed for a scanning operation. The shape of the actuator to be fabricated is stored in the scanning device of the laser ablation apparatus so that laser ablation proceeds along the outline of the actuator being fabricated so as to penetrate the SMA sheet 21. FIG. 14 shows an actuator fabricated by laser ablation, and FIG. 15 shows a portion thereof as enlarged. Use was made of a SMA sheet composed of TiNi SMA and having a thickness of 40 $\mu$m. The laser was used that has a wavelength of 775 nm, an output power of 0.01 mW/pulse, a pulse width of 150 fs, a repetition rate of 1 kHz and a spot diameter of 80 to 90 $\mu$m. As is apparent from FIGS. 14 and 15, it is seen that an actuator of a smooth and precision shape can be made. This method is advantageous in that it can accomplish fabrication practically in a single step without requiring a lithographic or etching step.

Figure 6:
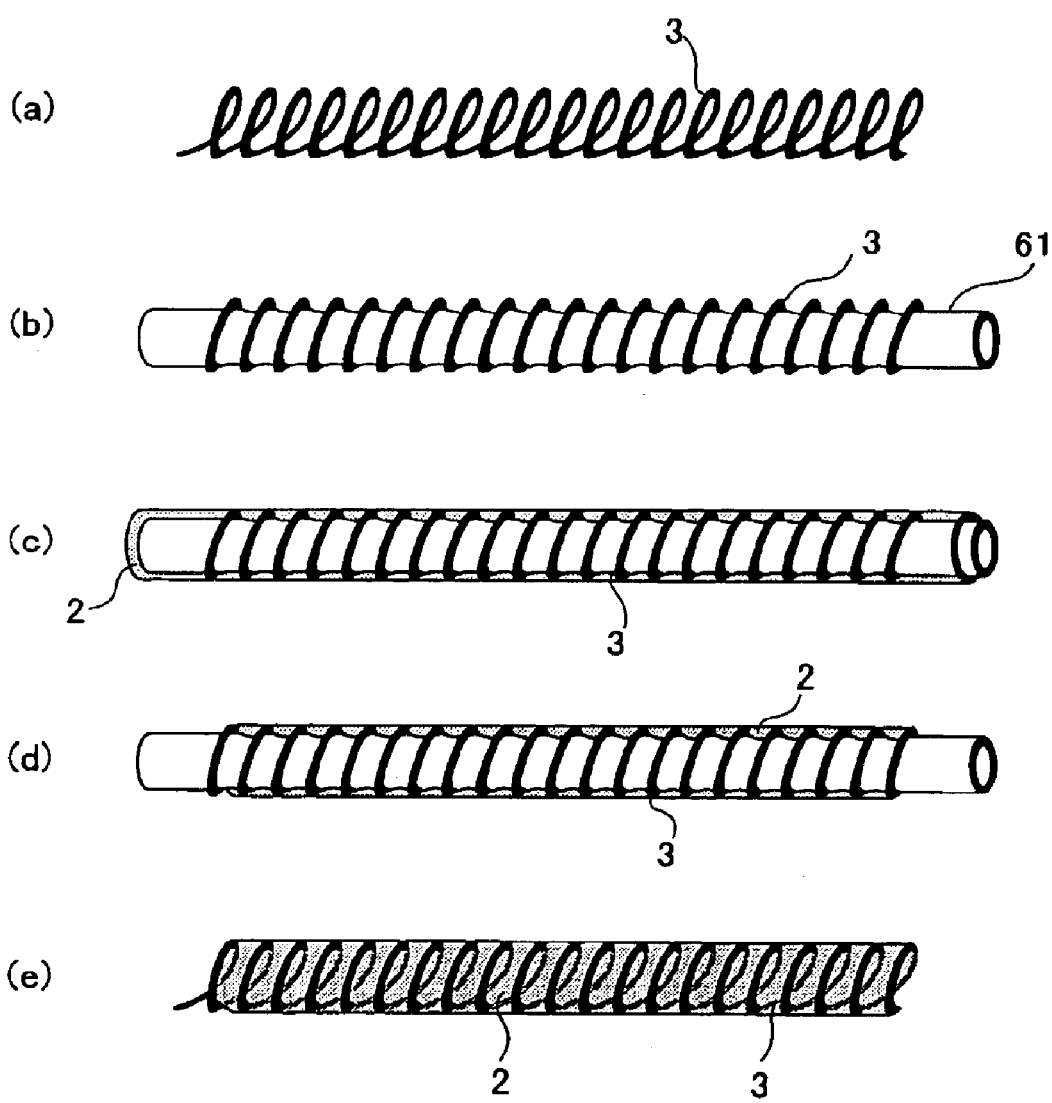
FIG. 6 is a flow chart illustrating a process of fabricating the outer tube in an active guide wire according to the present invention.
Figure 7:
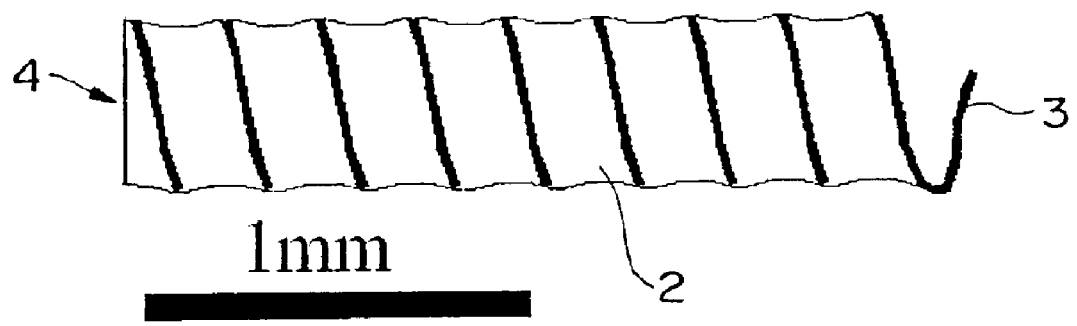
FIG. 7 is an enlarged view illustrating the outer tube thus fabricated.

Mention is next made of a method of fabricating the outer tube 4. Reference is made to FIG. 6 showing steps of fabricating an outer tube. In step (a), a coil 3 having an outer diameter, for example, of 0.46 mm is prepared, for example, from a stainless steel wire having a diameter of 0.05 mm. In step (b), a silicon tube 61 is fitted into the coil 3 to serve as a core therefor. In step (c) a liquid polyurethane is applied over the entire body of the coil 3 and the silicon tube 61, and in step (d) the applied polyurethane liquid 2 is dried. After both ends are cut off, removing the silicon tube 61 produces a tube of a bellows structure as the outer tube 4 in which the coil 3 is sheathed with a polyurethane coating 2 as shown in FIG. 6(e). The outer tube 4 thus fabricated is shown in FIG. 7 as enlarged, showing the bellows structure.

Figure 8:
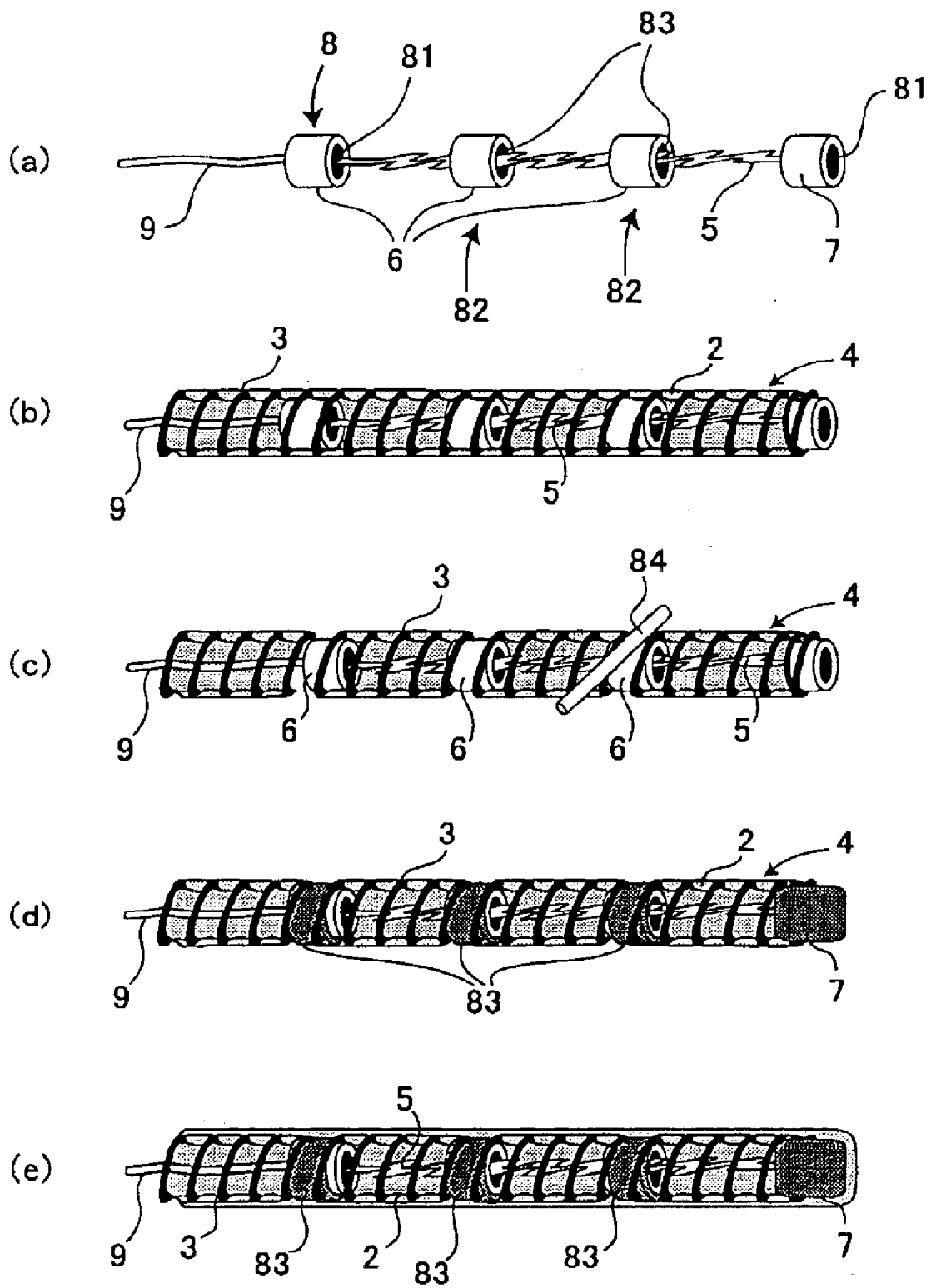
FIG. 8 is a flow chart shown in part perspective illustrating a procedure of assembling an active guide wire in accordance with the present invention.

Mention is next made of a process of assembling the active guide wire 1. Reference is had to FIG. 8 showing, in views in part perspective, a series of procedural steps of assembling an active guide wire according to the present invention.

In step (a) shown in FIG. 8, the leading end of the SMA actuator 5 is inserted into a brass pipe 7, which is then filled with room temperature setting, conductive epoxy resin 81 to fasten and electrically connect the leading end of the SMA actuator 5 to the brass tube 7. Next, glass pipes 6 and 6 are put over the SMA actuator 5 and positioned in intermediate regions 82 and 82 thereof, respectively. The glass pipes 6 and 6 are then filled with room temperature setting, nonconductive epoxy resin 83 to securely connect the intermediate regions 82 and 82 of the SMA actuator 5 to the glass tubes 6 and 6, respectively. Subsequently, another glass tube 6 is put over the SMA actuator 5 to locate at a base region 8 thereof, and after a lead conductor 9 that is an enamel wire of 0.07 mm in diameter is inserted into this glass tube 6, the latter is filled with room temperature setting, conductive epoxy resin 81 to securely connect and electrically connect the lead conductor 9 to the base region 8 of the SMA actuator 5 and to securely connect the base region 8 to the glass pipe 6.

In step (b) shown in FIG. 8, the SMA actuator 5 with these spacers and the lead conductor securely connected thereto is inserted into the outer tube 4.

Thereafter in step (c) shown in FIG. 8, those portions of the polyurethane coating 2 which lie over the glass pipes 6, 6 and 6 are melted off using an electrically heated wire 84 to form windows there.

In step (d) shown in FIG. 8, the windows are filled with room temperature setting, nonconductive epoxy resin 83 to securely connect the bias coil spring 3 to the glass pipes 6, 6 and 6. On the other hand, the brass tube 7 at the leading end of the active guide wire being formed is fastened and electrically connected to the bias coil spring 3 with room temperature setting, conductive epoxy resin 81.

Finally in step (e) shown in FIG. 8, a polyurethane solution 2 is applied over the outer tube 4 to smoothen its surface and at the same time to completely cover the bias coil spring 3 therewith, thereby ensuring its electrical insulation.

Figure 9:
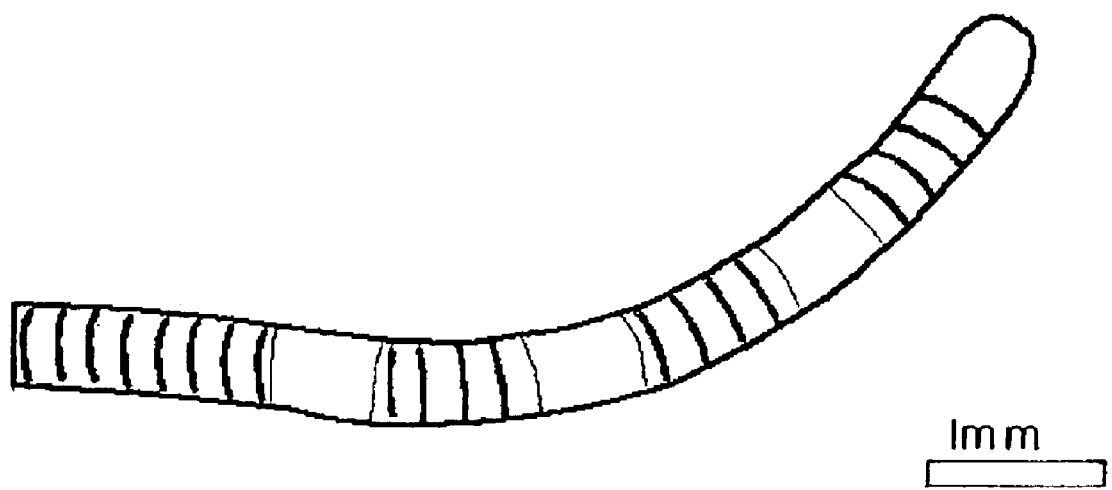
FIG. 9 is a view showing an active guide wire according to the present invention that is driven to bend in water at a temperature of 37° C.

Properties of an active guide wire so fabricated as mentioned above are described below. FIG. 9 is a view showing how the active guide wire according to the present invention is driven to bend in water at a temperature of 37° C. Use was made of an electric current of 120 mA in amount to drive the active guide wire.

Figure 10:
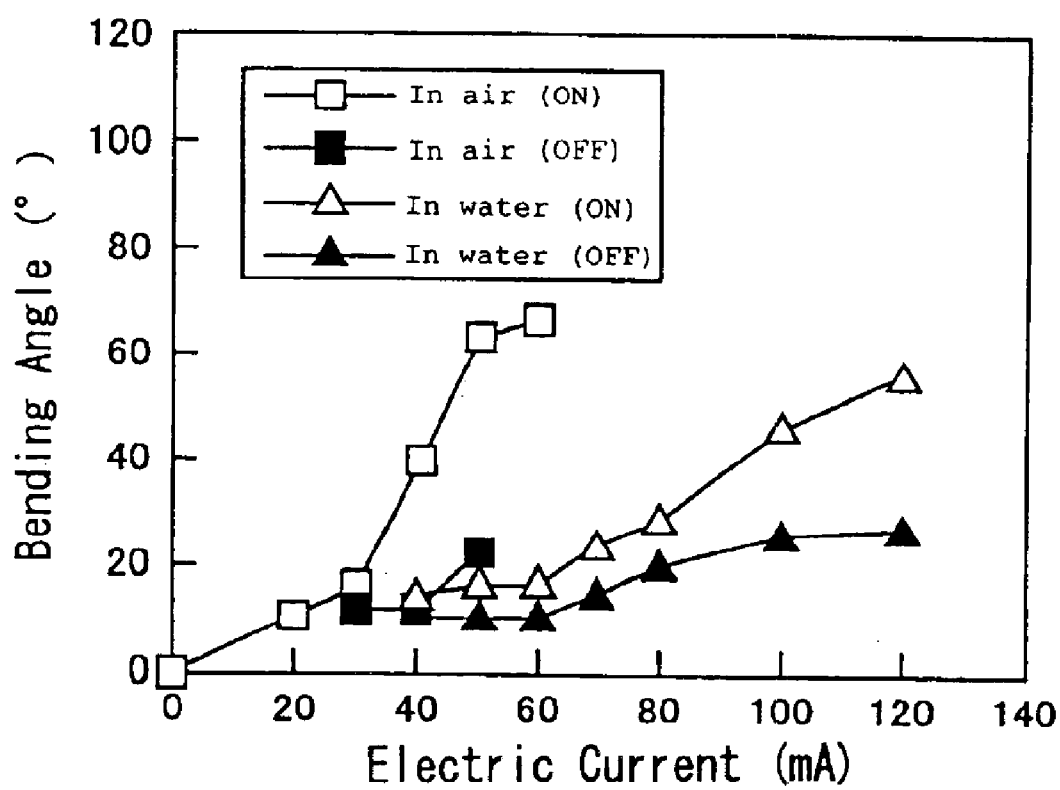
FIG. 10 is a graph showing the relationship between the electric current passed and the bending angle for an active guide wire according to the present invention when placed in air at a temperature 25° C. and in water at a temperature of 37° C.
Figure 11:
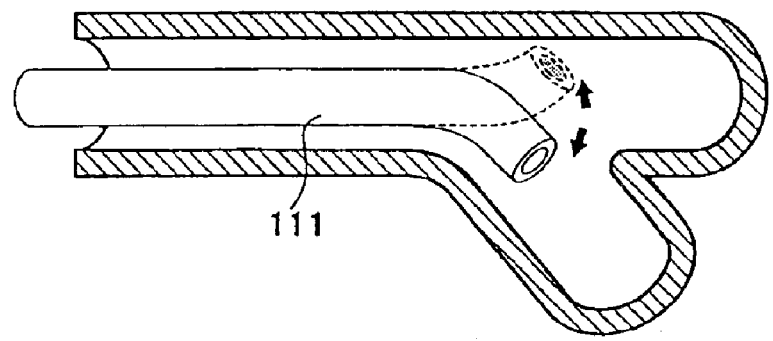
FIG. 11 is a diagrammatic view illustrating how a conventional active catheter is used.
Figure 12:
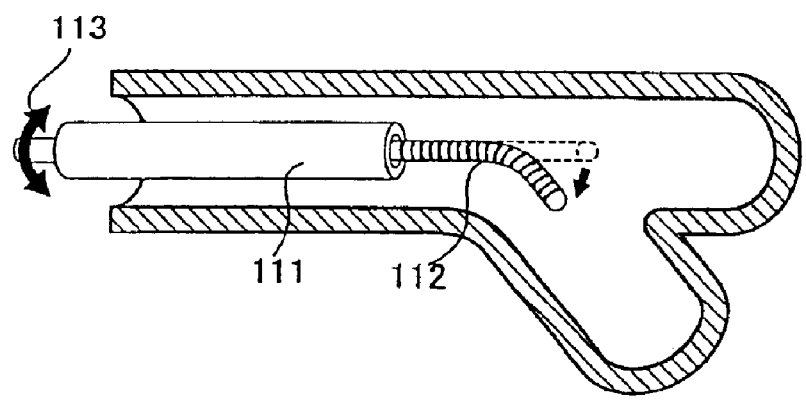
FIG. 12 is a diagrammatic view illustrating how another conventional active guide wire is used.
Figure 13:
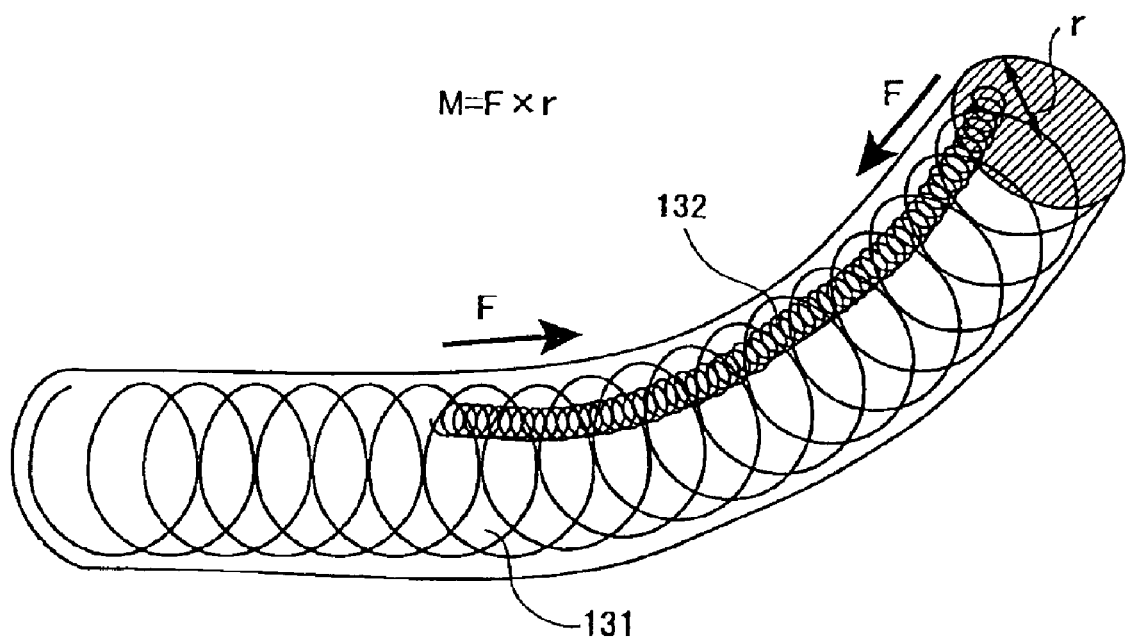
FIG. 13 is a diagrammatic view illustrating how another conventional active guide wire acts.

FIG. 10 is a graph showing relationship between the electric current passed through the SMA actuator to energize the active guide wire placed in the atmosphere at a temperature of 25° C. and in water at a temperature of 37° C. and the angle by which its leading end is then bent. In the graph, this bending angle is plotted along the ordinate and the energizing electric current is plotted along the abscissa. Plots indicated by □, ■, Δ and ▲ represent the bending angles where the active guide wire is energized in air, disenergized in air, energized in water and disenergized in water, respectively.

As is seen from the graph in FIG. 10, the leading end of the active guide wire was bent by 60° when it is energized and driven with an electric current of 50 mA in air. When driven in water, the active guide called for a greater amount of the energizing current than in air because of cooling effect by water; it has been found possible to reach a bending angle of 60° by increasing the electric current in amount. It has also been found that turning off the electric current to disenergize the active guide wire allows it to substantially restore its original state whether in air or in water.

Also, the active guide wire had a copper-constantan thermocouple of a wire diameter of 0.025 μm affixed thereto to measure its surface temperature. It has been found that in air the surface temperature rises nearly to 80° C. with an electric current of 50 mA, but in water the temperature rise is at most 42° C. apparently because of water's cooling effect. Accordingly, it has been proven that the active guide wire 1 fits well for use in the human body in which a similar cooling effect by the blood flow in the blood vessel is anticipated.

It has further been found that the active guide wire is remarkably tough against an external force. For example, it has been proven that repetitively bending it under an external force by an angle of 60° or more a large number of times makes practically no change in its properties. This appears to be due to the fact that the flat sheet shape memory alloy actuator according to the present invention is allowed to bend in a direction of the width of the bias coil spring and not to shrink axially of the bias coil spring, thereby preventing the latter from buckling.

As will be appreciated from the foregoing description, there is provided in accordance with the present invention an active guide wire that is not only small in diameter as required for the active guide wire used to carry a catheter in a narrow blood vessel of a complicate vascular system such as intracerebral and to guide it to reach a desired site for diagnosis or treatment, but also the adequate stiffness not to injure pathologically changed vascular walls. Thus, used in combination with a variety of existing catheters, such an active guide wire according to the present invention is anticipated to achieve great effects in the medical site where it is necessary to guide the catheter at will along a fine and fragile blood vessel in a complicate vascular system such as a pathologically changed cerebral blood vessel.

Although the present invention has been described in terms of the presently preferred form of embodiment, it is to be understood that such disclosure is purely illustrative and is not to be interpreted as limiting. Consequently, without departing from the spirit and scope of the invention, various alterations, modifications, and/or alternative applications of the invention will, no doubt, be suggested to those skilled in the art after having read the preceding disclosure. Accordingly, it is intended that the following claims be interpreted as encompassing all alterations, modifications, or alternative applications as fall within the true spirit and scope of the invention.

What is claimed is:

1. An active guide wire comprising: a bias coil spring; an outer tube having the bias coil spring sheathed therewith and providing an external wall for the active guide wire; and a shape memory alloy (SMA) actuator in the form of a flat sheet anchored in and securely connected to said outer tube, wherein said flat sheet SMA actuator is shape memorized so as to bend in a direction of the thickness of said flat sheet and has a shape running zigzag longitudinally thereof.

2. An active guide wire as set forth in claim 1 wherein said bias coil spring is composed of an electrically conductive elastic material.

3. An active guide wire as set forth in claim 1 wherein said outer tube is composed of a polymeric material.

4. An active guide wire as set forth in claim 1, further comprising an electrically conductive spacer whereby an end portion of said actuator and an end portion of said bias coil spring are brought together, a plurality of electrically nonconductive spacers whereby a plurality of intermediate regions of said actuator are fastened to a plurality of intermediate regions of said bias coil spring, respectively; a further electrically nonconductive spacer whereby a base portion of said actuator is fastened to a base portion of said bias coil spring; and a lead conductor connected to the base portion of said actuator.

* * * * *